United States Patent
He et al.

(10) Patent No.: US 10,160,710 B2
(45) Date of Patent: Dec. 25, 2018

(54) SYNTHESIS METHOD OF 3,4-HEXANEDIONE

(71) Applicant: HUAIYIN INSTITUTE OF TECHNOLOGY, Huai'an (CN)

(72) Inventors: Lei He, Huai'an (CN); Shan Yun, Huai'an (CN); Kun Hong, Huai'an (CN); Tan Guo, Huai'an (CN); Xiufang Zhu, Huai'an (CN); Jiadong Zhang, Huai'an (CN); Huaju Li, Huai'an (CN); Chaoyu Wang, Huai'an (CN); Jing Chen, Huai'an (CN); Ying Xu, Huai'an (CN)

(73) Assignee: HUAIYIN INSTITUTE OF TECHNOLOGY, Huai'an (CN)

( * ) Notice: Subject to any disclaimer, the term of this patent is extended or adjusted under 35 U.S.C. 154(b) by 0 days.

(21) Appl. No.: 16/050,851

(22) Filed: Jul. 31, 2018

(65) Prior Publication Data

US 2018/0334421 A1 Nov. 22, 2018

(30) Foreign Application Priority Data

Sep. 20, 2017 (CN) .......................... 2017 1 0858949

(51) Int. Cl.
*C07C 45/50* (2006.01)
*C07C 49/12* (2006.01)

(52) U.S. Cl.
CPC .............. *C07C 45/50* (2013.01); *C07C 49/12* (2013.01); *C07C 2531/02* (2013.01)

(58) Field of Classification Search
CPC ..................................................... C07C 45/50
See application file for complete search history.

(56) References Cited

U.S. PATENT DOCUMENTS

| 4,916,252 A | * | 4/1990 | Sayo ..................... C07C 29/145 560/122 |
| 5,349,107 A | * | 9/1994 | Watanabe ............... C07C 45/64 568/315 |

* cited by examiner

*Primary Examiner* — Sikarl A Witherspoon
(74) *Attorney, Agent, or Firm* — CBM Patent Consulting, LLC

(57) ABSTRACT

A synthesis method of 3,4-hexanedione comprises a step of 4-hydroxy-3-hexanonen oxidation, and in the step of 4-hydroxy-3-hexanonen oxidation, water is used as a catalyst, acetic acid is used as a cocatalyst, and ozone is used as an oxidizing agent to carry out an oxidation reaction on 4-hydroxy-3-hexanonen, and after the reaction, distillation under reduced pressure is carried out to obtain the 3,4-hexanedione. According to the synthesis method of 3,4-hexanedione in the invention, in the process of 4-hydroxy-3-hexanone oxidation, the 4-hydroxy-3-hexanone is placed in the water, the ozone is used for oxidation on the 4-hydroxy-3-hexanone, and the acetic acid is used as the cocatalyst, so that the entire oxidation reaction process is mild in conditions and simple to operate, no sewage is produced when the final product (3,4-hexanedione) is obtained, and the yield is greatly increased.

8 Claims, No Drawings

SYNTHESIS METHOD OF 3,4-HEXANEDIONE

This application claims priority to Chinese Patent Application Ser. No. CN201710858949.9 filed on 20 Sep. 2017.

TECHNICAL FIELD

The present invention relates to a synthesis method of 3,4-hexanedione, and belongs to the technical field of chemical product synthesis.

BACKGROUND ART 3,4-hexanedione, also known as dipropionyl, has a butter odor and can be used as a spice in beverages, frozen foods, candies, jellies and puddings. 3,4-hexanedione is also an important reaction intermediate and can be used for synthesis of furanone and other fine chemical products.

In currently widely used 3,4-hexanedione synthetic routes, during oxidation on 4-hydroxy-3-hexanone, oxidizing agents such as hydrated ferric sulfate, ferric chloride or Jones reagent are often used for oxidizing 4-hydroxy-3-hexanone to prepare 3,4-hexanedione. When this synthesis method is adopted to prepare a final product, a large amount of sewage which is difficult to dispose and degrade is generated, and great harm is brought to the environment.

SUMMARY OF THE INVENTION

Objective of the invention: the technical problem to be solved by the invention is to provide a synthesis method of 3,4-hexanedione; sewage is not produced when a final product is prepared through the method, the yield is greatly increased, and the problem that existing methods for preparing 3,4-hexanedione causes serious environmental pollution is effectively solved.

To solve the technical problem above, the technical scheme adopted by the invention is:

A synthesis method of 3,4-hexanedione. The method includes a step of 4-hydroxy-3-hexanone oxidation. In the step of 4-hydroxy-3-hexanone oxidation, water is used as a catalyst, acetic acid is used as a cocatalyst, and ozone is used as an oxidizing agent to carry out an oxidation reaction on 4-hydroxy-3-hexanone.

The synthesis method of 3,4-hexanedione specifically includes the following steps:

Step 1, propionaldehyde is used as a raw material to obtain 4-hydroxy-3-hexanone through condensation;

Step 2, the oxidation reaction is carried out on the 4-hydroxy-3-hexanone obtained in the step 1 to prepare the 3,4-hexanedione, wherein a required amount of the 4-hydroxy-3-hexanone is mixed with water, acetic acid is added, mixing and stirring uniformly are carried out, then ozone is introduced into a mixture to start the reaction, after the reaction, distillation under reduced pressure for separation is carried out to obtain 3,4-hexanedione.

More preferably, in the step 2, a mixing molar ratio of the 4-hydroxy-3-hexanone to the water to the acetic acid is: (0.3-0.4):1:(0.008-0.015).

Further preferably, in the step 2, a flow rate of the ozone is 0.25-0.35 L/min, and the flow rate of the ozone can ensure an appropriate reaction rate.

More preferably, in the step 2, reaction temperature is 5-15° C.; a too low reaction temperature may result in insufficient reactivity of reaction materials, and a too high reaction temperature may result in too fast decomposition of ozone and lowered solubility of ozone in water, so that generated ozonide is also unstable, and by-products are increased.

More preferably, in the step 2, after the oxidation reaction is completed, sodium bisulfite is added into a reaction system to remove a peroxide value.

The chemical reaction process of the synthesis method of 3,4-hexanedione in the invention is as follows:

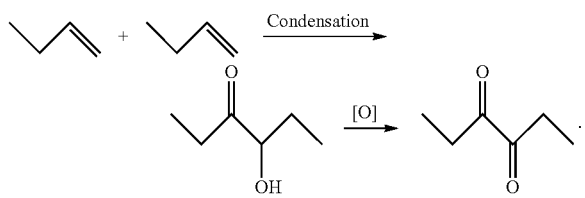

Compared with the prior art, the technical scheme of the invention has the following beneficial effects:

According to the synthesis method of 3,4-hexanedione in the invention, in the process of 4-hydroxy-3-hexanone oxidation, 4-hydroxy-3-hexanone is placed in water, ozone is used for oxidation on 4-hydroxy-3-hexanone, and acetic acid is used as a cocatalyst, so that the entire oxidation reaction process is mild in conditions and simple to operate, no sewage is produced when the final product (3,4-hexanedione) is obtained, and the yield is greatly increased; the synthesis method of the invention has the advantages of being green, safe and environmentally friendly.

DETAILED DESCRIPTION OF THE INVENTION

The technical scheme of the invention is further described in combination with following specific embodiments.

Embodiment 1

A step of 4-hydroxy-3-hexanone oxidation in a synthesis method of 3,4-hexanedione in the invention: first, 116.2 g of 4-hydroxy-3-hexanone (1 mol) and 41 g of water (2.5 mol) are added into a 500 mL three-necked flask for mixing, and then 1.5 g of acetic acid (0.025 mol) used as a cocatalyst is added into the three-necked flask; the three-necked flask is placed in a water bath pot for mixing and stirring by keeping at 5° C.; ozone is introduced into a mixture to carry out an oxidation reaction, a flow rate of the ozone is maintained at 0.3 L/min, and gas chromatography is used for tracking a reaction progress; after the reaction is completed, sodium bisulfite is added into a reaction system to remove ozone remaining in a solution (the ozone remaining in the solution is removed, and otherwise, residual ozone can continue to react to produce by-products during heating in a subsequent distillation process); finally distillation under reduced pressure for separation is carried out to obtain the finished product (3,4-hexanedione). With calculation of 4-hydroxy-3-hexanone, the yield of 3,4-hexanedione is 96.2% in the whole process.

Products obtained in the embodiment 1 include:
$^1$H NMR (400 MHz, CDCl$_3$): δ 2.78 (4H, q, 2-CH2-); δ 1.11 (6H, t, 2-CH$_3$).

Embodiment 2

A step of 4-hydroxy-3-hexanone oxidation in a synthesis method of 3,4-hexanedione in the invention: first, 116.2 g of 4-hydroxy-3-hexanone (1 mol) and 54 g of water (3 mol) are added into a 500 mL three-necked flask for mixing, and then 2.7 g of acetic acid (0.045 mol) used as a cocatalyst is added into the three-necked flask; the three-necked flask is placed in a water bath pot for mixing and stirring by keeping at 10° C.; ozone is introduced into a mixture to carry out an oxidation reaction, a flow rate of the ozone is maintained at 0.35 L/min, and gas chromatography is used for tracking a reaction progress; after the reaction is completed, sodium bisulfite is added into a reaction system to remove ozone remaining in a solution; finally distillation under reduced pressure for separation is carried out to obtain the finished product (3,4-hexanedione). With calculation of 4-hydroxy-3-hexanone, the yield of 3,4-hexanedione is 89.2% in the whole process.

Products obtained in the embodiment 2 include:

$^1$H NMR (400 MHz, CDCl$_3$): δ 2.78 (4H, q, 2-CH2-); δ 1.11 (6H, t, 2-CH$_3$).

Embodiment 3

A step of 4-hydroxy-3-hexanone oxidation in a synthesis method of 3,4-hexanedione in the invention: first, 116.2 g of 4-hydroxy-3-hexanone (1 mol) and 54 g of water (3 mol) are added into a 500 mL three-necked flask for mixing, and then 1.5 g of acetic acid (0.025 mol) used as a cocatalyst is added into the three-necked flask; the three-necked flask is placed in a water bath pot for mixing and stirring by keeping at 15° C.; ozone is introduced into a mixture to carry out an oxidation reaction, a flow rate of the ozone is maintained at 0.25 L/min, and gas chromatography is used for tracking a reaction progress; after the reaction is completed, sodium bisulfite is added into a reaction system to remove ozone remaining in a solution; finally distillation under reduced pressure for separation is carried out to obtain the finished product (3,4-hexanedione). With calculation of 4-hydroxy-3-hexanone, the yield of 3,4-hexanedione is 84.8% in the whole process.

Products obtained in the embodiment 3 include:

$^1$H NMR (400 MHz, CDCl$_3$): δ 2.78 (4H, q, 2-CH2-); δ 1.11 (6H, t, 2-CH$_3$).

In the synthesis method of 3,4-hexanedione in the invention, acetic acid is used as the cocatalyst, so that the solubility of ozone in water can be effectively increased (that is, acetic acid facilitates dissolution of ozone in water), and oxidizability of ozone can also be reduced (too high oxidizability of ozone may result in an increase in side reactions and the by-products), but if the acetic acid concentration is too high, the reactivity may be reduced, and if the acetic acid concentration is too low, the by-products may be increased; ozone needs to be dissolved in water to produce hydroxyl radicals with higher oxidizability to carry out a reaction, and therefore, in the method of the invention, water is used as both a solvent and a catalyst.

Comparative results of the yield of the finally prepared product 3,4-hexanedione and the amount of produced sewage between 4-hydroxy-3-hexanone oxidation modes selected in current 3,4-hexanedione synthesis techniques and a 4-hydroxy-3-hexanone oxidation mode selected in the 3,4-hexanedione synthesis technique in the invention are shown as Table 1:

TABLE 1

| | Reactants | Selected oxidizing agent | Yield of 3,4-hexanedione | Amount of sewage |
|---|---|---|---|---|
| Comparative embodiment 1 | acyl chloride, organic tin | metallic palladium as a catalyst | 45%-65% | high cost, much sewage |
| Comparative embodiment 2 | 4-hydroxy-3-hexanone | copper acetate as an oxidizing agent | 69% | much sewage |
| Comparative embodiment 3 | 4-hydroxy-3-hexanone | hydrogen peroxide/FeSO$_4$ as an oxidizing agent | 80% | much sewage |
| Comparative embodiment 4 | 4-hydroxy-3-hexanone | Jones reagent as an oxidizing agent | 30% | much sewage |
| Comparative embodiment 5 | 4-hydroxy-3-hexanone | ferric chloride as an oxidizing agent | 56% | much sewage |
| Embodiment 1 | 4-hydroxy-3-hexanone | ozone as an oxidizing agent | 96.2% | no sewage |

Table 1 shows that according to the synthesis method of 3,4-hexanedione in the invention, during oxidation of 4-hydroxy-3-hexanone, ozone is used for oxidation of 4-hydroxy-3-hexanone, and acetic acid is used as the cocatalyst, so that the entire oxidation reaction process is mild in conditions and simple to operate, not only is the yield of the product (3,4-hexanedione) greatly increased, but also no sewage is generated in the reaction process, and the problem of environmental pollution is effectively solved.

What is claimed is:

1. A synthesis method of 3,4-hexanedione, characterized in that the method comprises a step of 4-hydroxy-3-hexanone oxidation, and in the step of 4-hydroxy-3-hexanone oxidation, water is used as a catalyst, acetic acid is used as a cocatalyst, and ozone is used as an oxidizing agent to carry out an oxidation reaction on 4-hydroxy-3-hexanonen.

2. The synthesis method of 3,4-hexanedione according to claim 1, characterized in that a mixing molar ratio of the 4-hydroxy-3-hexanone to the water to the acetic acid is: (0.3-0.4):1:(0.008-0.015).

3. The synthesis method of 3,4-hexanedione according to claim 1, characterized in that a flow rate of the ozone is 0.25-0.35 L/min.

4. The synthesis method of 3,4-hexanedione according to claim 1, characterized in that the method specifically comprises the following steps:
   step 1, propionaldehyde is used as a raw material to obtain 4-hydroxy-3-hexanone through condensation; and
   step 2, the oxidation reaction is carried out on the 4-hydroxy-3-hexanone obtained in the step 1 to prepare the 3,4-hexanedione, wherein a required amount of the 4-hydroxy-3-hexanone is mixed with the water, acetic acid is added, mixing and stirring uniformly are carried out, then the ozone is introduced into a mixture to start the reaction, and after the reaction, distillation under reduced pressure for separation is carried out to obtain the 3,4-hexanedione.

5. The synthesis method of 3,4-hexanedione according to claim 4, characterized in that in the step 2, a mixing molar ratio of 4-hydroxy-3-hexanone to the water to the acetic acid is: (0.3-0.4):1:(0.008-0.015).

6. The synthesis method of 3,4-hexanedione according to claim 4, characterized in that in the step 2, a flow rate of the ozone is 0.25-0.35 L/min.

7. The synthesis method of 3,4-hexanedione according to claim 4, characterized in that in the step 2, reaction temperature is 5-15° C.

8. The synthesis method of 3,4-hexanedione according to claim 4, characterized in that in the step 2, after the oxidation reaction is completed, sodium bisulfite is added into a reaction system to remove ozone remaining in a solution.

\* \* \* \* \*